United States Patent [19]

Libit

[11] 4,011,242
[45] Mar. 8, 1977

[54] PROSTAGLANDIN INTERMEDIATES AND PROCESSES FOR PREPARATION OF PROSTAGLANDIN INTERMEDIATES

[76] Inventor: Lawrence Libit, 240 E. O'Keefe St., Palo Alto, Calif.

[22] Filed: Jan. 6, 1975

[21] Appl. No.: 539,027

Related U.S. Application Data

[62] Division of Ser. No. 230,939, March 1, 1972, Pat. No. 3,859,188.

[52] U.S. Cl. .................. 260/340.3; 260/340.9; 260/514 D
[51] Int. Cl.[2] ........................... C07D 319/08
[58] Field of Search ................ 260/340.3

Primary Examiner—Anton H. Sutto
Assistant Examiner—Michael Shippen
Attorney, Agent, or Firm—Wallenstein, Spangenberg, Hattis & Strampel

[57] ABSTRACT

Preparation of prostaglandins and certain intermediates therefor wherein a 1,5-diene compound such as

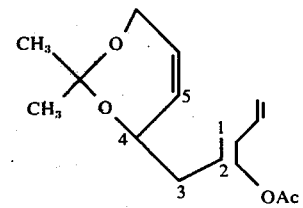

is subjected to a photochemical chemical reaction in the presence of a photosensitizer whereby to effect ring closure with the conversion to a bicyclo [2.1.1] system followed by conversion to intermediates such as

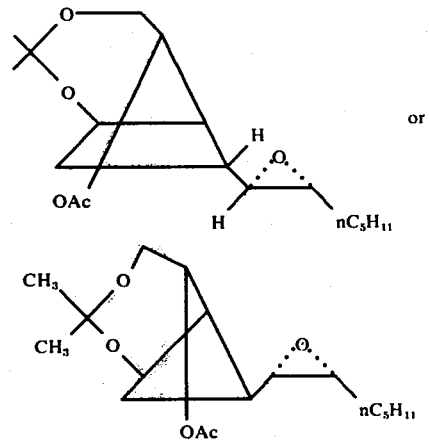

The resulting intermediate is subsequently fragmented to produce a further intermediate having stereochemistries such as are present in prostaglandins which, in turn, is converted by known techniques into prostaglandins.

6 Claims, No Drawings

PROSTAGLANDIN INTERMEDIATES AND PROCESSES FOR PREPARATION OF PROSTAGLANDIN INTERMEDIATES

This is a division of application Ser. No. 230,939, filed Mar. 1, 1972 now U.S. Pat. No. 3,859,188, dated Jan. 7, 1975.

My invention is directed to the preparation of prostaglandins and is particularly concerned with certain improvements in the process of preparing the same.

Prostaglandins are important pharmaceutical products and have utility for a variety of purposes including their use as abortive agents. A number of said prostaglandins have the 20-carbon atom skeleton found in prostanoic acid. Many of the prostaglandins, and various methods for their preparation, are shown in one or more of U.S. Pat. Nos. 3,435,053; 3,505,386; 3,505,387; 3,524,867 and 3,598,858.

For illustrative purposes and by way of simplification of explanation of my invention, which is described below, two of the known prostaglandins are shown below in terms of their structural configuration:

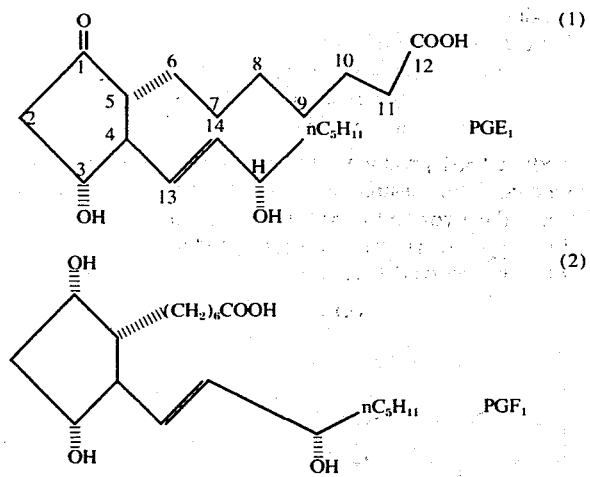

The so-called E type (i.e. $E_1$) contains four significant structural features: (a) a $\beta$-hydroxy ketone, the hydroxyl having a specific stereochemical relationship to substituents at C-4 and C-5; (b) a $C_7$ carboxylic acid side chain that is cis to C-3 hydroxyl and trans to the C-5 allylic alcohol side chain; (c) an allylic alcohol side chain at C-4 that contains a trans disubstituted double bond, the side chain being trans to the C-5 chain and trans to the C-3 hydroxyl; and (d) centers of optical activity exist at C-3, C-4, C-5, and C-15. Furthermore, the stereochemistries of the C-3, C-4, and C-5 substituents in $PGE_1$ permit two arrangements that are d and l optical enantiomers and, thus, the ring and its substituents at C-3, C-4 and C-5 may be defined as an optical unit of D or L chirality. Since the allylic C-15 hydroxyl may have a d or l optical configuration, there are four (Dd; Dl; Ld; Ll) enantiomers of structure $E_1$. The F type is a formal reduction product of the E series.

So far as I am aware, previously known synthetic routes to the preparation of prostaglandins, in their introduction of the aforementioned structural features into the prostaglandin molecules, have, in the main, involved the utilization of reactions which are difficult to carry out even though, to at least a considerable extent, they have utilized many classical synthetic procedures. Indeed, only recently has it apparently been possible to selectively introduce the aforesaid feature (d) into the molecule (E. J. Corey et al, J. Am. Chem. Soc., 92, 2586 (1970), and reference cited therein).

My present invention results in materially simplifying the preparation of prostaglandins, in which all four of the aforementioned structural features are introduced. Furthermore, it results in the production of a common key intermediate (3), shown below, from which all of the prostaglandins of the E and F series can be produced.

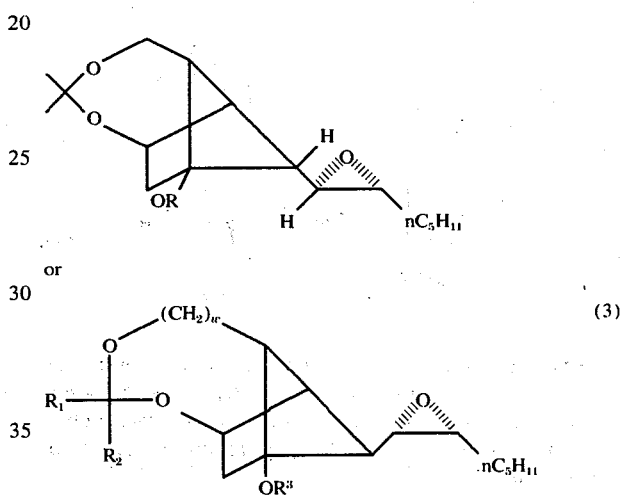

where $R_1$ and $R_2$ are the same or different alkyl or cycloalkyl or aralkyl groups containing up to 8 carbon atoms, illustrative examples of which are methyl, ethyl, n-propyl, isopropyl, n-butyl, isobutyl, tert-butyl, n-amyl, isoamyl, n-hexyl, isohexyl, n-pentyl, isopentyl, n-octyl, isooctyl, cyclopropyl, cyclopentyl, cyclohexyl, cyclooctyl, or benzyl. It is particularly preferred that $R_1$ and $R_2$ both be methyl. $R_3$ is acyl, particularly lower monocarboxylic acyl such as acetyl, propionyl or butyryl but it can also be of aromatic or araliphatic character such as benzoyl or cyclohexylacetyl, particularly preferred being acetyl. Moreover, the OAc radical at the $C_3$ position can be replaced by a $CH_2$-X radical where X is halogen, notably chlorine or bromine. The integer w can range from 1 to 10, preferably being 1.

In the practice of the process of my invention, the aforementioned intermediate (3) is produced and said intermediate is then transformed to prostaglandins of types E and F, all as is described below.

Before describing the particulars with respect to the process of my present invention, it may be pointed out that the aforementioned structural features (a), (b) and (c) are achieved through the utilization of the aforesaid intermediate (3). The reactions pursuant to which the aforesaid structural features (a), (b) and (c) are introduced into the molecule are shown below:

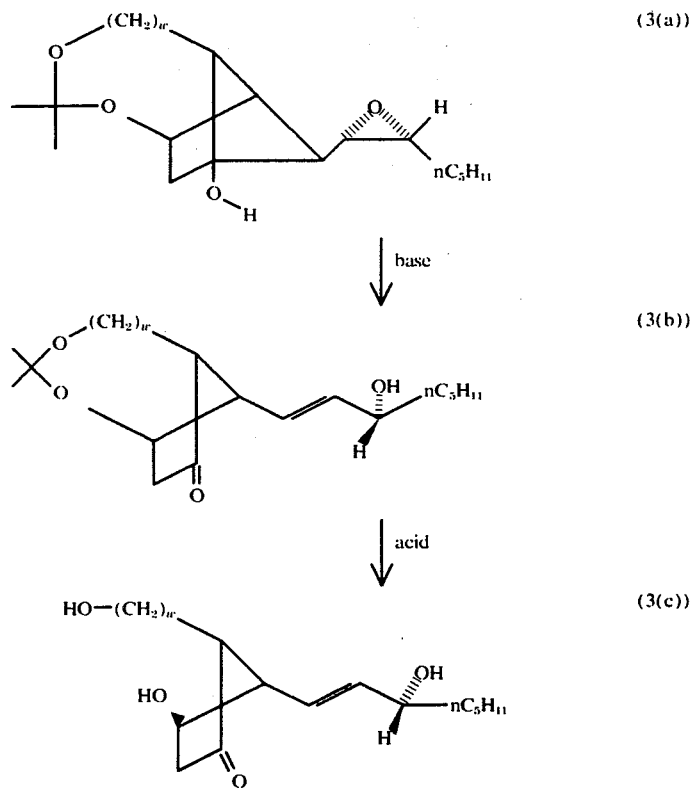

Where the intermediate is in the form of a compound where the C-3 position is occupied by a CH₂-X radical as aforesaid, then, upon reduction with a metal such as zinc, for instance, the following reaction occurs, as illustrated below

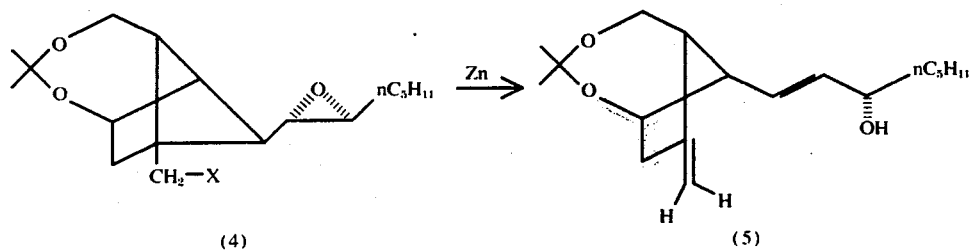

which shows the results of a variant form of the 1,4 fragmentation step.

In view of the foregoing, it is clear that a base catalyzed opening (or any 1,4 fragmentation reaction that gives 4) of product (3a) produces product (4) or its formal acid hydrolysis product, intermediate product (5)), which has configurations at C-15, C-4 and C-5 that correspond to geometric relationships present on the five membered ring in the E type prostaglandins. In particular, the concerted ring opening of the epoxide in product (3a) produces the trans disubstituted double bond and the desired allylic C-15 hydroxyl. Furthermore, the hydroxyl is produced with a single sense of chirality (d or l), provided that product (3a) has been optically resolved (the approach described here has a provision for the specific introduction of two optical centers with a single resolution). When the OH attached to the side chain at C-5 is formally oxidized to an acid, prostaglandin E₁ is obtained as shown below:

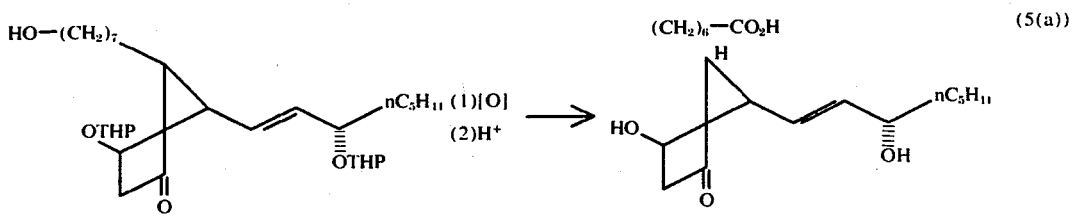

In the following illustrative example of the production of intermediate compound (3), compound (6) is initially subjected to intramolecular photochemical cyclization by ultraviolet light in the presence of a photosensitizing agent as, for instance, benzophenone, as shown below:

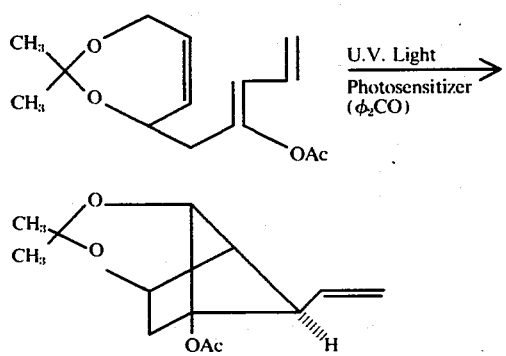

extent or degree of the introduction of structural feature (d), namely, the control of optical activity at the C-15 position. In other words, where a mixture of the (7a) and (7b) compounds is utilized, dl mixture is created at the C-15 position, whereas, if the mixture of (7a) and (7b) has been optically resolved (e.g. pure D or pure L chirality in the bicyclic structure), there is obtained a dl mixture of a single prostaglandin. Where compounds (7a) and (7b) are produced selectively with resolution into their respective D and L (D and L refer to bicyclic structure) forms, the application of the foregoing reactions result in the production of pure optical (d or l) isomers of the prostaglandins and all optical isomers of the prostaglandins can be produced, as is outlined below:

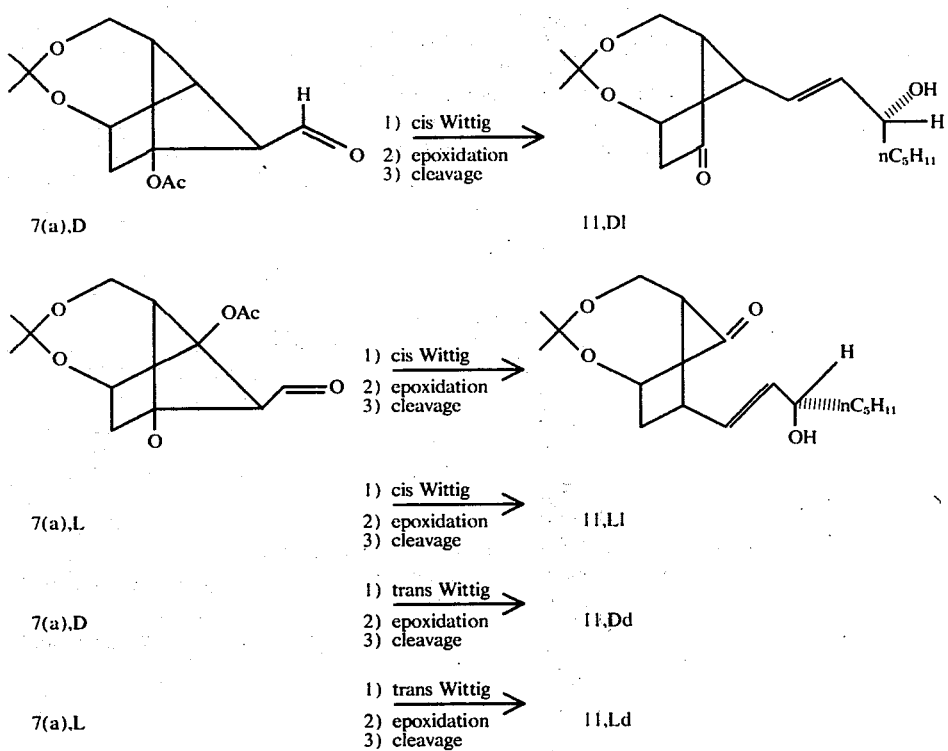

The aforesaid intermediate (7a) or (7b) is advantageously optically resolved into its d or l form by hydrolysis to its respective alcohol, followed by ester formation with an optically active acid and subsequent separation by procedures which are, per se, known to the art to produce predominately the (7a) or the (7b) compound, as the case may be. It is, however, unnecessary to make this separation since it bears only upon the It is clear, from the foregoing, that, using compound (7b) (D or L), the same products are obtained (Dl, Ll, Dd, Ld) by means of the foregoing transformations provided 7b prefers the conformation shown below and epoxidations are anti to the acetate.

Ozonolysis of compounds 7a and/or 7b is then carried out which results in the production of the corresponding aldehydes 8a and 8b, respectively as shown below:

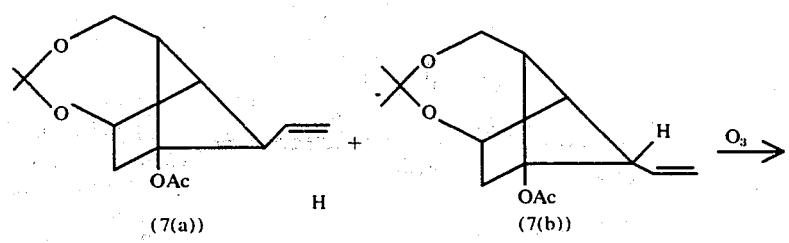

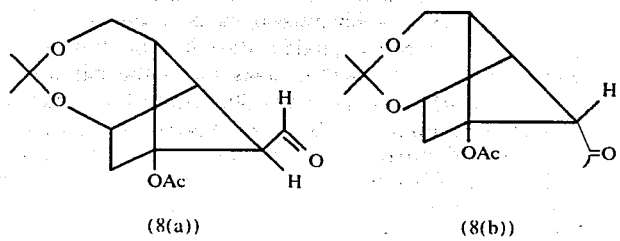

(8(a))    (8(b))

If desired, any mixture of aldehydes 8a and 8b can be equilibrated to produce essentially exclusively aldehyde 8a or aldehyde 8b, as the case may be. For purposes of discussion and convenience, reference is made below to the treatment of aldehyde 8a, except in references pertaining to structural feature (d).

The aldehyde 8a is next treated with a selective Wittig reagent to produce a cis or trans double bond, as desired, in accordance with known procedures (E. J. Corey et al, J. Am. Chem. Soc., 91, 5675 (1969)). Where the cis disubstituted olefinic compound 9a is produced, as shown below.

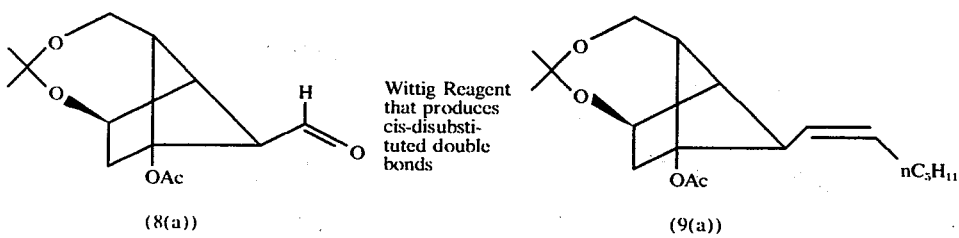

(8(a))    (9(a))

said compound 9a is then reacted with a hindered peracid, such as 2,6-dimethyl-3-chloroperbenzoic acid. The attack on the least hindered side of compound 9a occurs with the formation of epoxide compound 10a, as shown below:

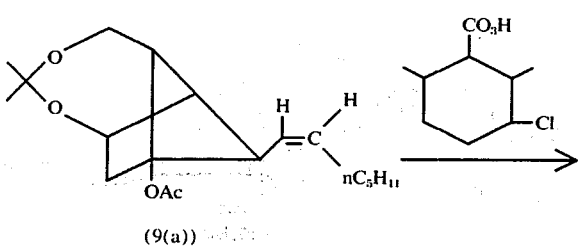

(9(a))

-continued

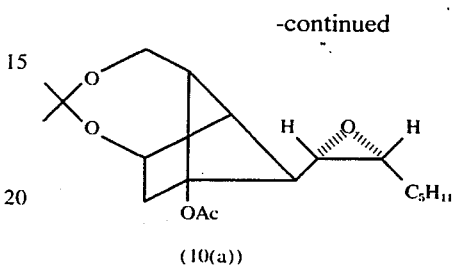

(10(a))

In place of the acetate, other organic carboxylic acids can be used as, for instance, propionic acid, tert-butyl carboxylic acid and benzoic acid.

Next, compound 10a (which is equivalent to intermediate compound 3) is base catalyzed fragmented to produce essentially the single isomer 11a (intermediate 5), as shown below:

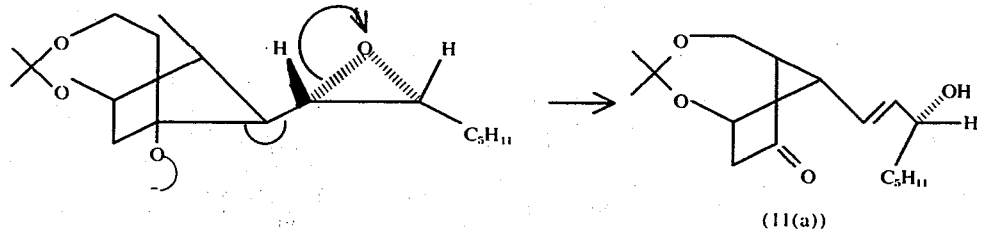

(11(a))

In view of the foregoing, it will be seen that the fragmented compound 11a contains the structural features (a), (b), (c) and (d); that, since the bicyclic ring system has been optically resolved, compound 10a is an optically active compound whose epoxide is anti to the ester; the 1,4 fragmentation is presumably a concerted process requiring "back-side attack," and, thus, a trans double bond is formed with a single chirality (d or l) at the C-15 position. One can produce the same selectivity from a syn epoxide and front side displacement.

The conversion of compound 11a to prostaglandins of the E and F series is then carried out in any one or more of the manners described below.

In the case of the synthesis of prostaglandin $E_1$ ($PGE_1$), for instance, starting with intermediate 3, the following series of reactions can be carried out, utilizing procedural techniques which are, per se, known to the art:
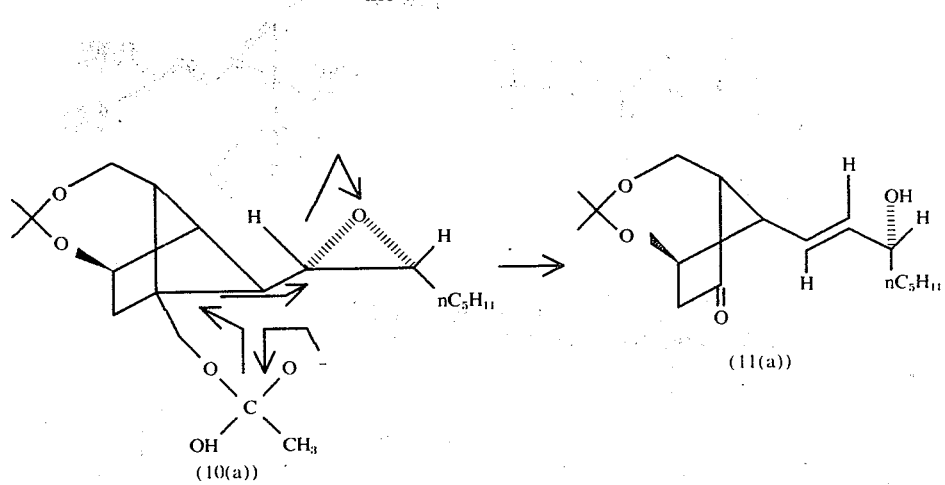
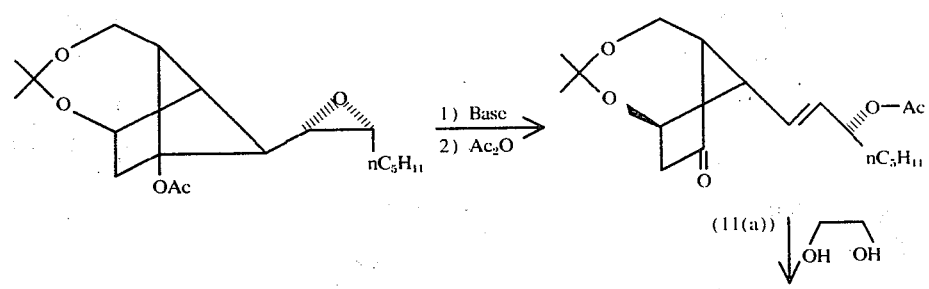
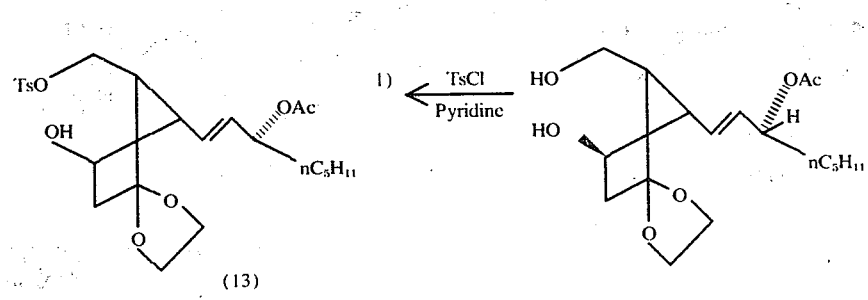
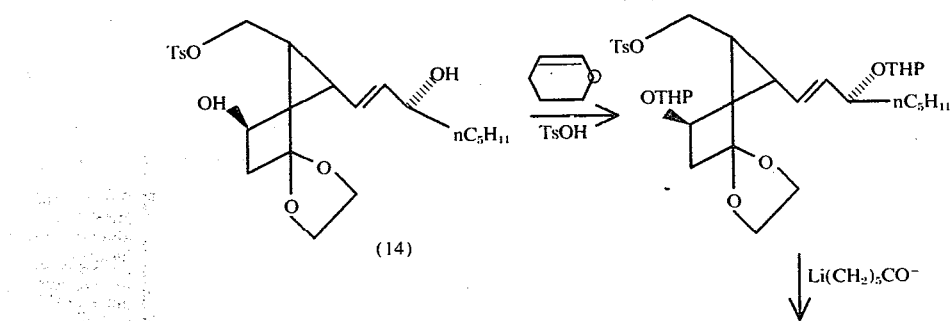

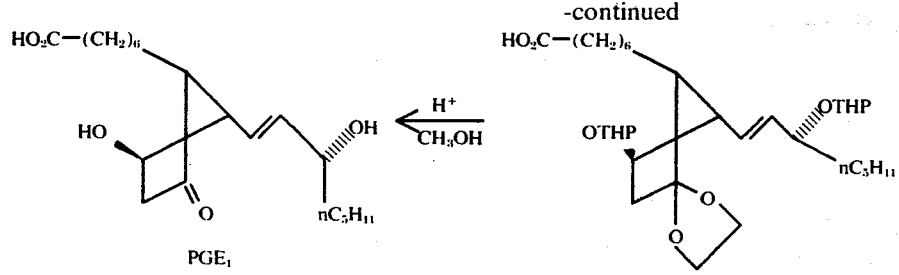
PROCEDURE 1
A simple variant or modification of the sequence in Procedure 1 results in the synthesis of PGE$_2$, thusly:
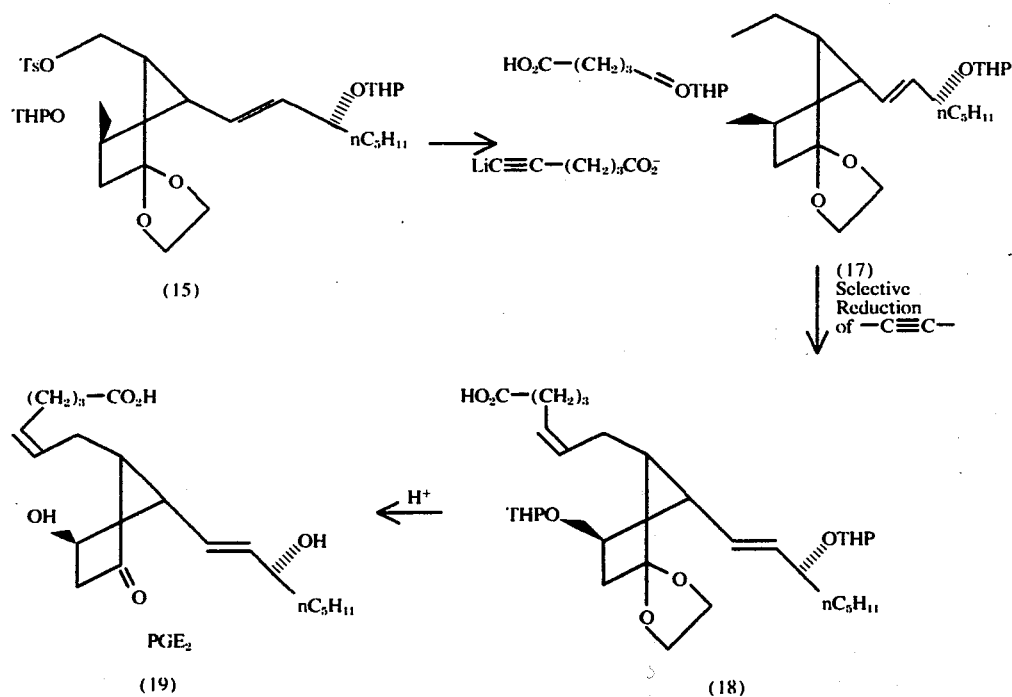
Similarly, still another variation or modification of the sequence of Procedure 1 results in the production of PGE$_3$.
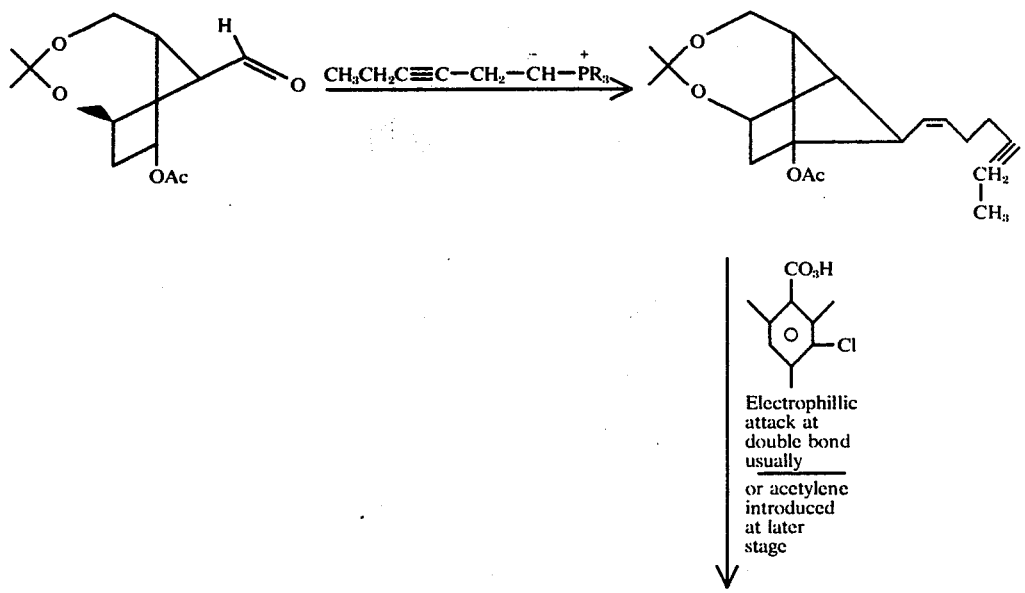

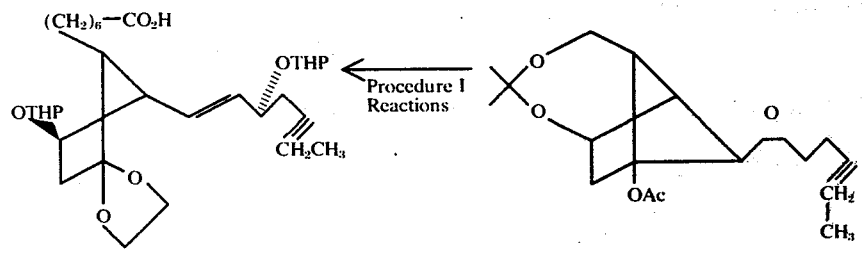
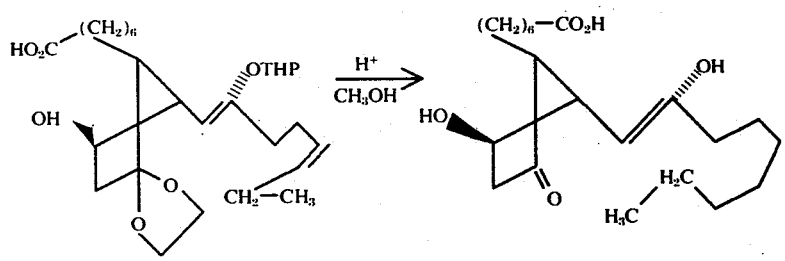
For the synthesis of the F series of prostaglandins, the following variation or modification of Procedure 1 results in the production of the prostaglandin $F_1a$:
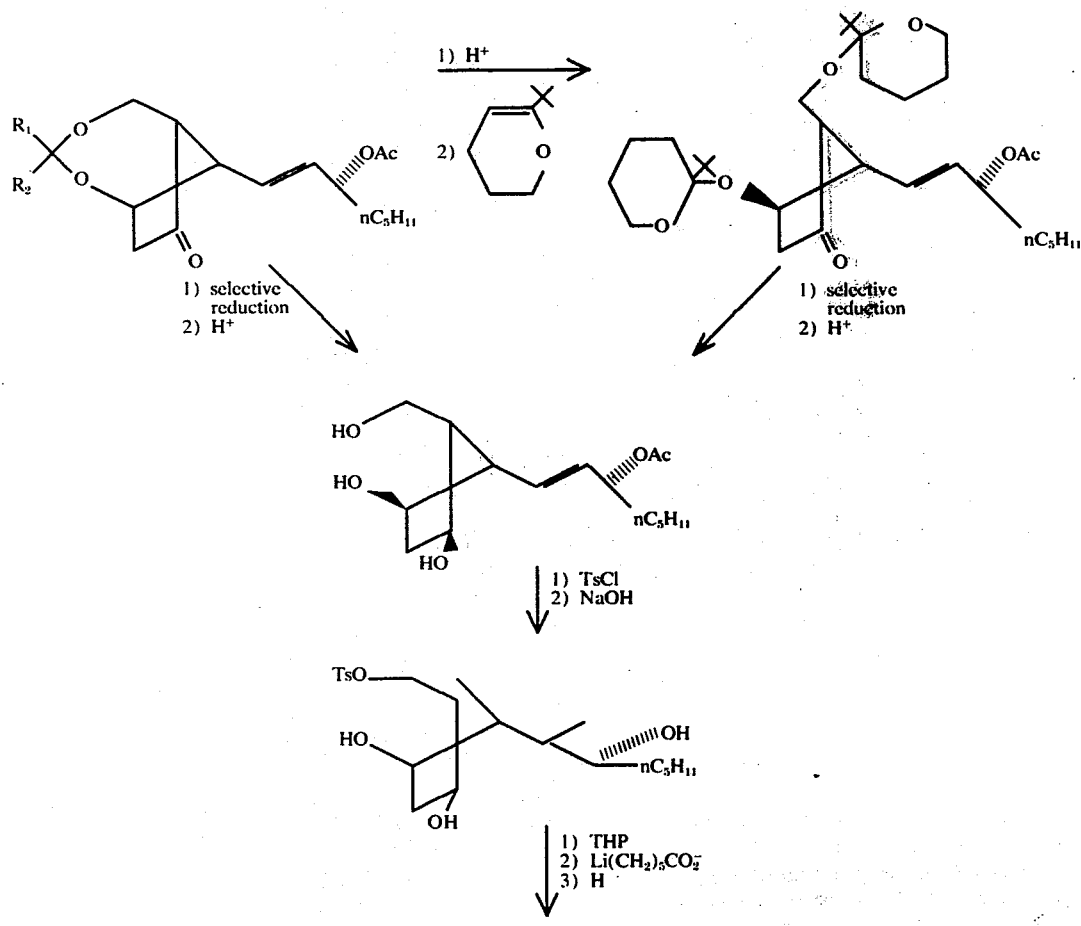

-continued

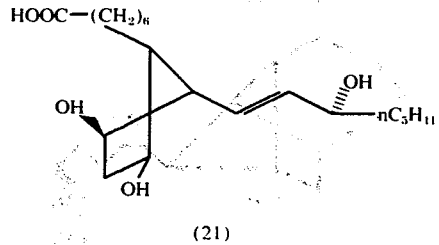
(21)

The selective reduction of compound 21 can be achieved by the introduction of a large group at the C–3 hydroxyl to create the most unfavorable 1,3 diaxial interaction in the molecule.

The reactions described in Procedure 1 and the variants and modifications thereof represent illustrative procedures, the aforedescribed photocyclization reaction and the 1,4-fragmentation reaction from a preferred conformation representing the essential procedures since these two reactions set up and produce the desired stereochemical relationships found in the prostaglandins. The conversion of the intermediates derived from the photocyclization 1,4-fragmentation reaction sequence involves simply the application of heretofore known reactions.

The above described intermediate 3 can be converted to prostaglandins by other procedures, per se known to the art, as shown by the following series of reactions:

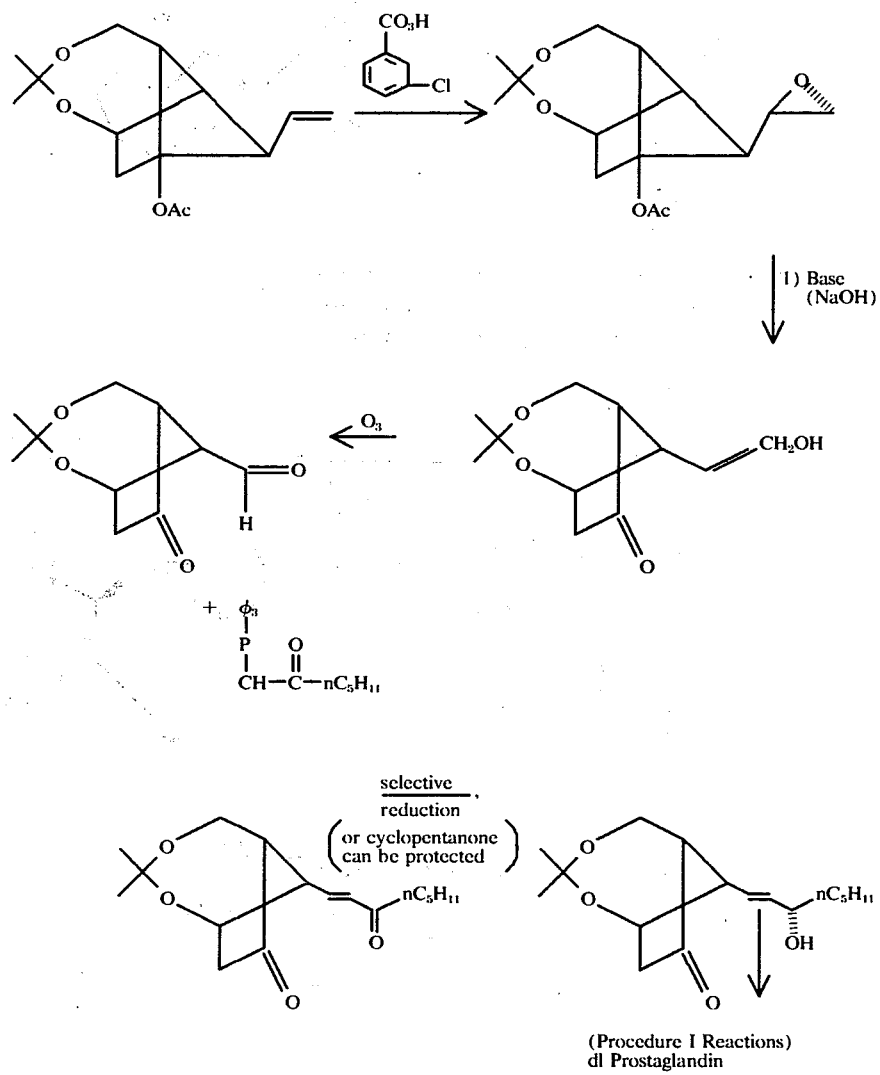
(Procedure I Reactions)
dl Prostaglandin

Various modifications can be made from intermediate 3 to produce keto-aldehyde derivatives thereof which can, in turn, be converted by known procedures to various prostaglandins.

The following examples are illustrative of procedures, utilizing the foregoing teachings, for the production intermediate 3 and the utilization of said intermediate 3 in the synthesis of derivatives thereof leading to the production of prostaglandins. The said examples are not to be construed as limitative of my invention since various other procedures can be utilized by the skilled chemist in the light of and based upon the teachings which I have provided. All parts given are by weight.

tanoic acid derivatives, notably prostaglandins, in which the key features comprise (1) the photochemical ring closure of a 1,5-diene as illustrated below

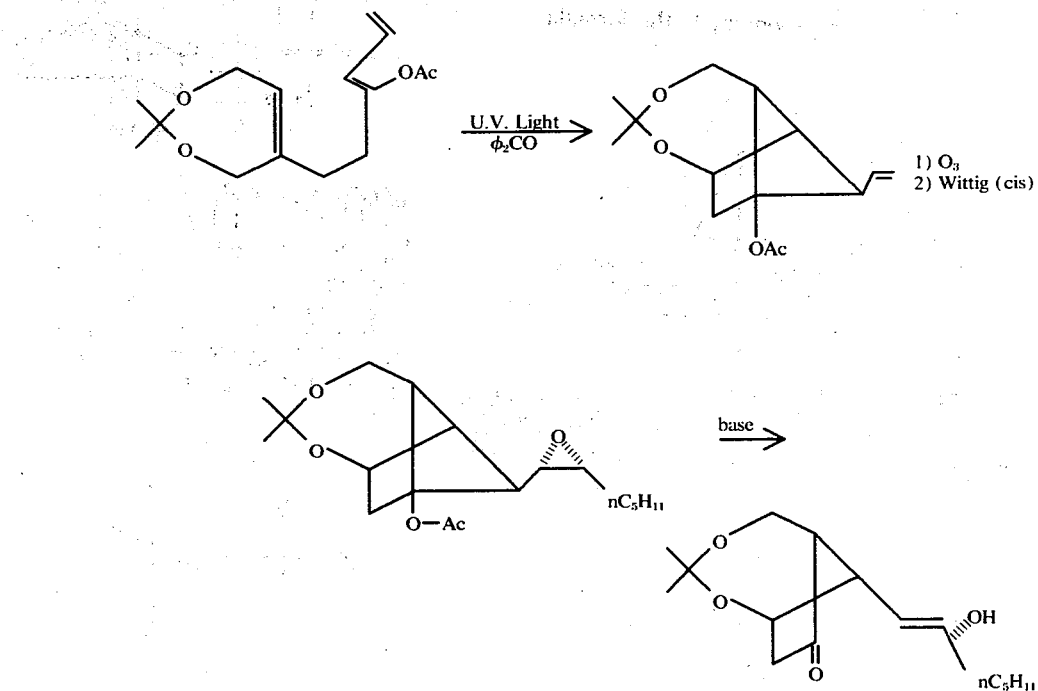

EXAMPLE

1. Photocyclization of Intermediate 6.

A solution of 10 parts of compound (6) and 5 parts of benzophenene in 1000 parts of pentane is irradiated (high pressure Hanovia Type L lamp fitted with a Pyrex filter) under argon at 0°–5° C for 10 hours. The solvent is removed at reduced pressure and the photocyclized product isolated by chromatography on silica gel. The resulting photocyclized product (7) is characterized by spectral analysis (IR, NMR and mass spectroscopy).

2. Epoxidation of Intermediate 7.

To a solution of 9.5 parts of compound 6 in methylene chloride there is added 6.5 parts m-chloroperbenzoic acid at 0°–5° C. After 4 hours at room temperature the epoxide (3d) is isolated by extraction with ether, the ether being washed with 20 parts of saturated sodium bicarbonate solution and dried over anhydrous magnesium sulfate. The epoxide (3d) is characterized by spectral analysis as referred to above.

3. Cleavage of the Epoxide to Keto-Alcohol 4d.

To a solution of 9 parts of the epoxide (3d) in 100 parts of methanol there is added, under nitrogen, a solution of 1.32 parts of sodium hydroxide in 50 parts of water. After 1 hour at room temperature, the solution is diluted with 500 parts of ether and the water is separated. The ether is washed with saturated sodium chloride solution, dried over anhydrous sodium sulfate, filtered and concentrated to obtain the keto-alcohol (4d). The keto-alcohol (4d) is characterized by the aforesaid spectral analysis techniques.

In summary, it will be seen that my present invention is concerned with a process for the synthesis of prostanoic acid derivatives, notably prostaglandins, in which the key features comprise (1) the photochemical ring closure of a 1,5-diene as illustrated below to a bicyclo[2.1.1] system which is converted to key intermediate 3, a β-acetoxy-epoxide whose stereochemistry is controlled by the steric restraints present in the photoproduct (4); followed by (2) 1,3 fragmentation of the 3a product which results in an intermediate whose stereochemistries are exactly those found in the prostaglandins of the E and F series. Optical resolution of photoproduct 4 can be effected, if desired, and when the resolved product is subjected to the said 1,3-fragmentation procedure, subsequent conversion is effected by known methods to the prostaglandins whereby pure d or l prostaglandins are selectively produced.

In the photochemical ring closure reaction, while benzophenone has been disclosed as a preferred photosensitizer in the reaction to produce intermediate compound 3, various other photosensitizers can be utilized.

I claim:

1. The process for the preparation of intermediates useful in the production of prostaglandins, the steps which comprise subjecting a compound corresponding to the formula

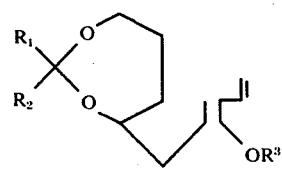

where $R_1$ and $R_2$ are the same or different alkyl, cycloalkyl or aralkyl groups containing up to 8 carbon atoms, and $R^3$ is acyl, selected from the group consisting of acetyl, propionyl, butyryl, benzoyl and cyclohexylacetyl, to irradiation in the presence of a photosensitizing agent to effect photocyclization of said compound, and then epoxidizing said photocyclized compound to produce a compound corresponding to the formula

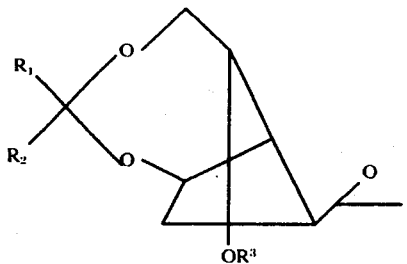

2. The process of claim 1, in which the epoxidized compound is then cleaved to produce a keto-alcohol corresponding to the formula

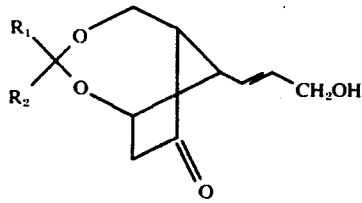

3. A chemical compound corresponding to the formula

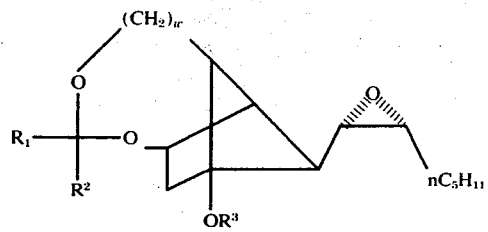

where $R_1$ and $R_2$ are the same or different alkyl or cycloalkyl or aralkyl groups containing up to 8 carbon atoms, $R^3$ is a member selected from the group consisting of acetyl, propionyl, butyryl, benzoyl and cyclonexylacetyl and w is an integer from 1 to 10.

4. A chemical compound in accordance with claim 3, in which $R_1$ and $R_2$ are each methyl.

5. A chemical compound

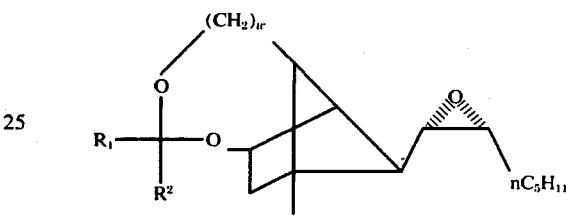

where $R_1$ and $R_2$ are the same or different alkyl or cycloalkyl or aralkyl groups containing up to 8 carbon atoms, $R^3$ is acetyl, and w is an integer from 1 to 10.

6. A chemical compound in accordance with claim 5, in which w is 1.

* * * * *